(12) United States Patent
Matsuoka et al.

(10) Patent No.: US 6,458,963 B1
(45) Date of Patent: *Oct. 1, 2002

(54) PROCESS FOR PREPARING EPROSARTAN USING REGIOSELECTIVE PROTECTION OF 2,4-DISUBSTITUTED-IMIDAZOLE INTERMEDIATES

(75) Inventors: Richard T. Matsuoka; Peng Liu, both of Norristown, PA (US)

(73) Assignee: SMithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,604

(22) Filed: Aug. 14, 2001

Related U.S. Application Data

(62) Division of application No. 09/355,186, filed as application No. PCT/US98/02411 on Feb. 13, 1998, now Pat. No. 6,294,675.
(60) Provisional application No. 60/038,196, filed on Feb. 14, 1997.

(51) Int. Cl.$^7$ .............................................. C07D 333/22
(52) U.S. Cl. ..................................................... 548/315.1
(58) Field of Search ....................................... 548/315.1

(56) References Cited

U.S. PATENT DOCUMENTS

| | | |
|---|---|---|
| 5,185,351 A | 2/1993 | Finkelstein et al. |
| 5,418,250 A | 5/1995 | Finkelstein et al. |
| 5,444,080 A | 8/1995 | Girard et al. |

FOREIGN PATENT DOCUMENTS

| | | |
|---|---|---|
| EP | 0 403 159 A2 | 6/1990 |
| WO | WO 92/10189 | 6/1992 |

OTHER PUBLICATIONS

Keenan, et al., J. Med. Chem., 1993, vol. 36, pp. 1880–1892, abstract No. XP–002100935.
Keenan, et al., J. Med. Chem., 1992, vol. 35, pp. 3858–3872, abstract No. XP–002153508.
Shilcrat, et al., J. Med. Chem., 1997, vol. 62, pp. 8449–8454, abstract No. XP–002153509.

*Primary Examiner*—Joseph K. McKane
*Assistant Examiner*—Rebecca Anderson
(74) *Attorney, Agent, or Firm*—Laura K. Madden; Mary E. McCarthy; Charles M. Kinzig

(57) ABSTRACT

The present invention relates to a process for preparing eprosartan, an angiotensin II receptor antagonist useful in the treatment of hypertension, congestive heart failure, and renal failure. The process for preparing eprosartan consists of three stages. These stages are: (Stage†1) the regioselective protection of 2-n-butyl-4-formylimidazole; (Stage†2) the reaction between the product from Stage 1 and (2-thienylmethyl)-propanedioic acid, mono-$C_{1-4}$alkyl ester; and (Stage†3) quaternary salt formation, followed by a basic work-up and an acidification. The efficiency of this synthetic sequence is particularly is particularly useful for the large-scale production of eprosartan.

4 Claims, No Drawings

PROCESS FOR PREPARING EPROSARTAN USING REGIOSELECTIVE PROTECTION OF 2,4-DISUBSTITUTED-IMIDAZOLE INTERMEDIATES

This is a divisional of application Ser. No. 09/355,186, filed Jul. 27, 1999, now U.S. Pat. No. 6,294,675, which is a 371 of International Application Ser. No. PCT/US98/02411, filed Feb. 13, 1998, which claims priority to U.S. Provisional application Ser. No. 60/038,196, filed Feb. 14, 1997.

FIELD OF THE INVENTION

The present invention relates to a process for preparing eprosartan. This compound is described in U.S. Pat. No. 5,185,351 as being an angiotensin II receptor antagonist useful in the treatment of hypertension, congestive heart failure and renal failure.

BACKGROUND OF THE INVENTION

U.S. Pat. No. 5,185,351 describes processes for the preparation of imidazole compounds, in particular the preparation of eprosartan. Although the processes described in this patent produce the imidazoles claimed therein, there was a need to improve these processes when preparing compounds, such as eprosartan, on a commercial scale.

It has now been found that eprosartan can be prepared in three stages. These stages are: (Stage†1) the regioselective protection of 2-n-butylformylimidazole; (Stage†2) the reaction between the product from Stage 1 and (2-thienylmethyl)-propanedioic acid, mono-$C_{1-4}$alkyl ester; and (Stage†3) quaternary salt formation, followed by a basic work-up and an acidification. The efficiency of this synthetic sequence and the quality and yield of eprosartan are particularly important when preparing said product on a large scale for therapeutic use.

DESCRIPTION OF THE INVENTION

The present invention provides a process for the preparation of eprosartan, which is (E)-α-[[2-butyl-1-[(4-carboxyphenyl)methyl]-1H-imidazol-5-yl]methylene]-2-thiophene propanoic acid, a compound of formula (I):

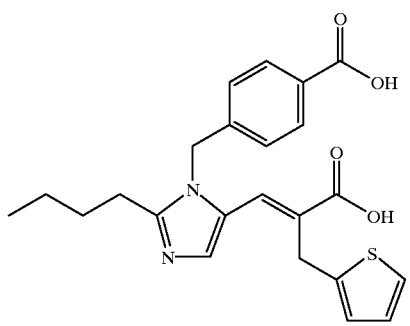

or a pharmaceutically acceptable salt thereof,
which process comprises the steps of:

(i) treating a compound of formula (II):

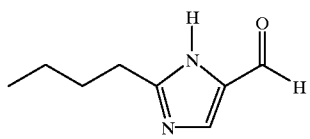

with base, followed by reaction with a regioselective nitrogen-protecting reagent, such as a $C_{1-4}$alkyl ester derivative of acrylic acid;

(ii) reacting the compound of formula (III):

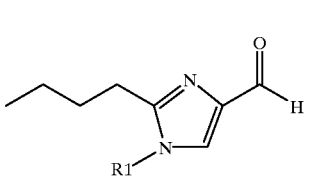

wherein R1 is a nitrogen protecting group either consisting of (1) an ethylene bridge connecting the nitrogen to an electron-withdrawing group, such as an ester (COOR", where R"=$C_{1-4}$alkyl), acid, carbonyl, nitrile, sulfone, or sulfoxide, or (2) a methylene bridge connecting the nitrogen to a pivalate, 2-(trimethylsilyl)ethoxy, methoxy, tert-butoxy, or benzyloxy, with a compound of formula (IV):

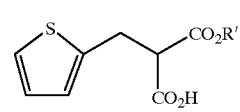

wherein R' is $C_{1-4}$alkyl, in the presence of a catalyst; and
(iii) reacting the compound of formula (V):

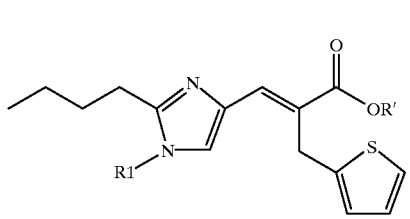

wherein R' and R1 are as defined above, with a compound of formula (VI):

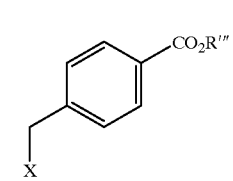

wherein R'" is $C_{1-4}$alkyl and X is halo or OR*, in which R* is $CH_3SO_2$— or p-$CH_3C_6H_4SO_2$—, at elevated temperatures;
and thereafter removing the N–3 protecting group and hydrolyzing the R' and R'" ester group, and optionally forming a pharmaceutically acceptable salt.

Acid addition salts of formula (I) are formed with the appropriate inorganic or organic acids by methods known in the art. Representative examples of suitable acids are maleic, fumaric, acetic, succinic, hydrochloric, hydrobromic, sulfuric, phosphoric or methanesulfonic. Preferably, the pharmaceutically acceptable acid addition salt for the formula (I) compound is the methanesulfonic acid addition salt.

Base addition salts of formula (I) are formed with the appropriate inorganic or organic bases by methods known in the art. Cationic salts are prepared by treating the parent compound with an excess of an alkaline reagent, such as hydroxide, carbonate or alkoxide, containing the appropriate cation; or with an appropriate organic amine. Representative examples of cations are $Li^+$, $Na^+$, $K^+$, $Ca^{++}$, $Mg^{++}$ and $NH_4^+$.

As used herein, $C_{1-4}$alkyl means an alkyl group of 1–4 carbons, branched or unbranched. $C_{1-4}$alkyl includes methyl, ethyl, n-propyl, isopropyl, n-butyl, isobutyl and t-butyl. The preferred R' $C_{1-4}$alkyl group is ethyl, the preferred R" $C_{1-4}$alkyl group is ethyl or methyl and the preferred R'" $C_{1-4}$alkyl group is ethyl or methyl.

Scheme I, below, summarizes the three stages of the novel synthetic pathway used to prepare eprosartan.

SCHEME I

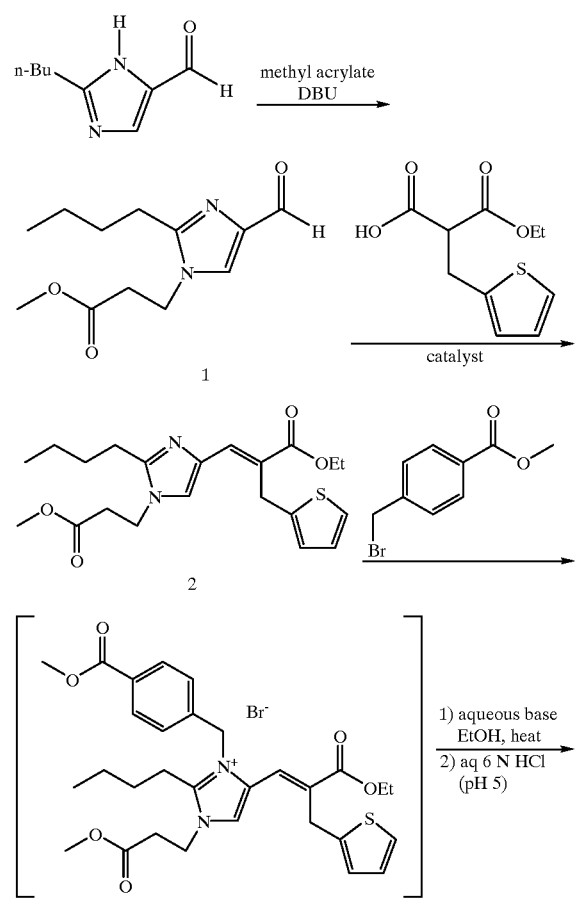

According to Scheme I, 2-n-butyl-4-formylimidazole is treated with a base, such as 1,8-diazabicyclo[5.4.0]undec-7-ene (DBU) or 1,1,3,3-tetramethylguanidine, followed by reaction with a regioselective nitrogen-protecting reagent, such as methyl acrylate, ethyl acrylate, acetyl bromide, chloromethyl pivalate (POM-Cl) or di-tert-butyl dicarbonate, to give derivatization on the least hindered nitrogen atom of the imidazole ring. This reaction can be carried out in ethyl acetate, acetonitrile, toluene, DMF, THF or 1-methyl-2-pyrrolidinone (NMP). Preferably, this reaction is carried out using DBU and methyl acrylate or ethyl acetate in ethyl acetate at 50–60° C. Typically, the Scheme I-1 compound is then reacted with (2-thienylmethyl) propanedioic acid, monothyl ester in a suitable solvent, such as toluene, acetonitrile, DMF, THF, NMP, or DMSO, in the presence of a catalyst, for example, in the presence of piperidine or piperidinium propionate in excess propionic acid, at a suitable temperature, such as a temperature of about 70° C. to about 100° C. Preferably, this reaction is carried out using piperidine in toluene at a reflux temperature of 65° C.–70° C.; this reflux temperature is obtained by placing the reaction mixture under reduced pressure. The quaternary salt of the Scheme I-2 compound is then prepared by reacting this compound with a benzyl halide, such as methyl or ethyl 4-(bromomethyl)benzoate, or a benzyl mesylate or tosylate at elevated temperatures, for example, at temperatures of 100–120° C., preferably at 105–110° C. The ester groups are hydrolyzed and the N-protecting group is removed using, for example, base, such as aqueous sodium or potassium hydroxide, to give eprosartan (Scheme I-3). Thereafter, pharmaceutically acceptable salts may be prepared as described above.

Alternately, eprosartan can be prepared as summarized in Scheme II, below.

SCHEME II

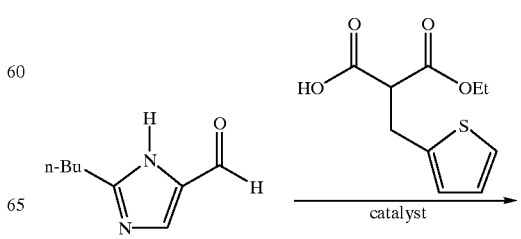

EXAMPLES

Example 1

Preparation of (E)-α-[[2-Butyl-1-[(4-carboxyphenyl)-methyl]-1H-imidazol-5-yl]methylene]-2-thiophene propanoic acid (Eprosartan)

Stage†1: Preparation of

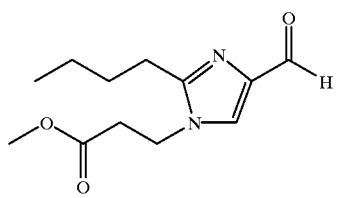

A heterogeneous solution of 2-n-butyl-4-formylimidazole (155.0 kg, 1018 mol) in ethyl acetate (775.0 L) was treated at room temperature with methyl acrylate (131.5 kg, 1527 mol) followed with 1,8-diazabicyclo[5.4.0]undec-7-ene (DBU, 7.75 kg, 50.9 mol). The reaction mixture was then heated to 50–60° C. (the mixture became completely homogeneous when heated) and stirred at that temperature until the reaction was complete (approximately 2 hours). The excess methyl acrylate and the ethyl acetate were distilled off under vacuum, maintaining the base temperature below 60° C. The residual bronze-colored oil, containing the above-noted Stage 1 product, was diluted with toluene (1033 L) and was used in the next step without further purification.

Stage†2: Preparation of

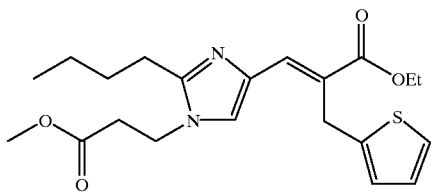

The crude Stage 1 product from above was treated with (2-thienylmethyl)-propanedioic acid, mono-ethyl ester (267.3 kg @ 100%, 1171 mol) and piperidine (21.7 kg, 255 mol). The resulting solution was heated to reflux (65–70° C.) under reduced pressure; the water produced during the reaction was removed by the Dean-Stark method. Reflux was continued until the reaction was complete (approximately 2–3 hours). The reaction mixture was cooled to 55–60° C. and was washed with a 20% w/w brine solution (485.3 L) and demineralised water (485.3 L) to remove much of the piperidine catalyst. The toluene was then removed by vacuum distillation, maintaining the base temperature below 60° C. The residual bronze-colored oil, containing the Stage 2 product, was used in the next step without further purification.

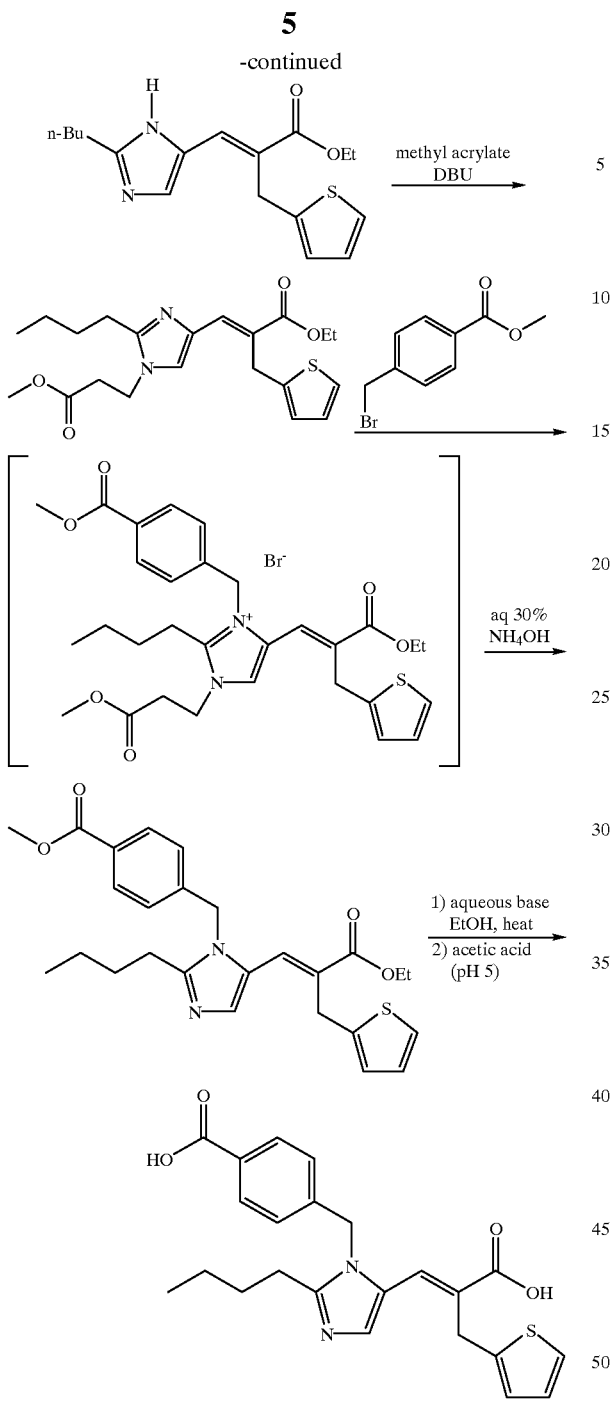

According to Scheme II, the order of the first and second steps detailed in Scheme I have been reversed. In this synthetic sequence, 2-n-butyl-4-formylimidazole is reacted with (2-thienylmethyl)propanedioic acid, mono-ethyl ester in the presence of a catalyst, and then the product from this reaction is regioselectively N-protected. Quaternization and basic work-up is carried out as detailed in Scheme I to give eprosartan.

Also included in the scope of the present invention are the novel intermediates used in the preparation of eprosartan. These intermediates are described hereinbefore.

The invention is illustrated by the following example. The example is not intended to limit the scope of this invention as defined hereinabove and as claimed hereinbelow.

Stage 3: Preparation of

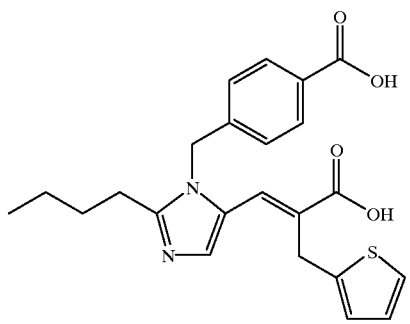

The residual oil containing the crude Stage 2 product was diluted with toluene (583.0 L). The resulting solution was treated with solid methyl 4-(bromomethyl)-benzoate (291.6 kg @ 100%, 1273 mol) and was subsequently stirred at 70–75° C. for 30 minutes to ensure that a homogeneous solution was obtained. The toluene was distilled off under vacuum, maintaining the process temperature between 60 and 75° C. The resulting thick oil was heated at 95–100° C. until the reaction was shown to be complete (approximately 6–10 hours). The reaction mixture was cooled to 75–80° C. and diluted with IMS (ethanol containing 1% v/v MeOH, 1534.0 L). An aqueous solution of sodium hydroxide [203.7 kg (5093 mol) dissolved in demineralised water (936.0 L)] was prepared and added to the ethanolic solution of the intermediate quaternary salt. The mixture was heated to reflux (approximately 80° C.) and reflux was continued until the hydrolysis to the title compound was complete (approximately 2 hours). The reaction mixture was cooled to 50–60° C. and treated with aqueous 6 N hydrochloric acid solution (approximately 479.0 L, 2874 mol) until a pH of 5.1 to 5.3 was achieved. The resulting slurry was cooled to 10–15° C. and was held at that temperature for approximately 2 hours to complete the precipitation. The slurry was filtered and the wet cake was washed with 50% v/v aqueous IMS (approximately 520 L) and water (approximately 1790 L) to afford 344.9 kg (estimated 66.9% yield over the three stages) of the title compound as a beige-colored wet solid.

It is to be understood that the invention is not limited to the embodiment illustrated hereinabove and the right to the illustrated embodiment and all modifications coming within the scope of the following claims is reserved.

What is claimed is:

1. A process for the preparation of eprosartan, a compound of formula (I):

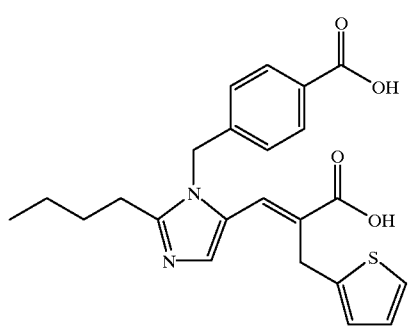

(I)

or a pharmaceutically acceptable salt thereof, which process comprises the steps of:

(i) treating a compound of formula (II):

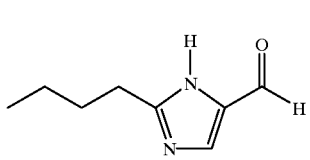

(II)

with base, followed by reaction with a regioselective nitrogen-protecting reagent;

(ii) reacting the compound of formula (III):

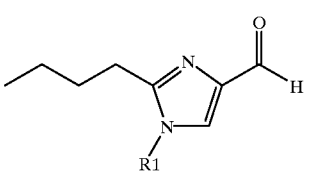

(III)

wherein R1 is a nitrogen protecting group either consisting of (1) an ethylene bridge connecting the nitrogen to an electron-withdrawing group, selected from the group consisting of an ester (COOR", where R"=$C_{1-4}$alkyl), acid, carbonyl, nitrile, sulfone, and sulfoxide, or (2) a methylene bridge connecting the nitrogen to a pivalate, 2-(trimethylsily)ethoxy, methoxy, tert-butoxy, or benzyloxy, with a compound of formula (IV):

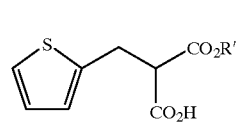

(IV)

wherein R' is $C_{1-4}$alkyl, in the presence of a catalyst; and (iii) reacting the compound of formula (V):

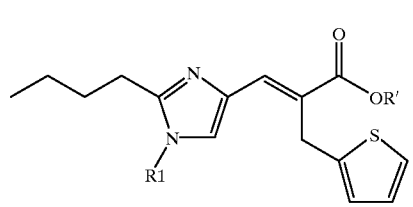

(V)

wherein R' and R1 are as defined above, with a compound of formula (VI):

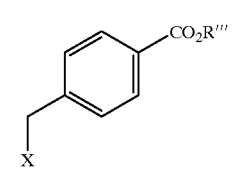

(VI)

wherein R'" is $C_{1-4}$alkyl and X is halo or OR*, in which R* is $CH_3SO_2$- or p-$CH_3C_6H_4SO_2$-, at elevated temperatures; and thereafter hydrolyzing the R' and R'" ester groups and removing the N–3 protecting group, and optionally forming a pharmaceutically acceptable salt.

2. The process according to claim 1 for the preparation of eprosartan, a compound of formula (I):

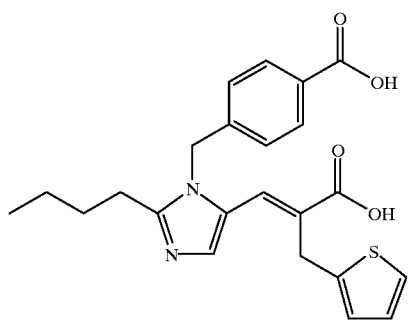
(I)

or a pharmaceutically acceptable salt thereof, which process comprises the steps of:

(i) treating a compound of formula (II):

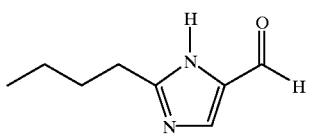
(II)

with base, followed by reaction with a $C_{1-4}$alkyl ester derivative of acrylic acid;

(ii) reacting the compound of formula (IIIb):

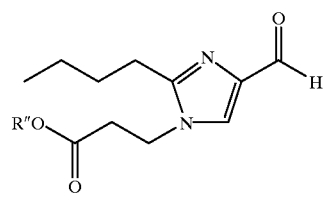
(IIIb)

wherein R" is $C_{1-4}$alkyl, with a compound of formula (IV):

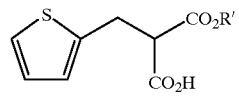
(IV)

wherein R' is $C_{1-4}$alkyl, in the presence of a catalyst; and (iii) reacting the compound of formula (Vb):

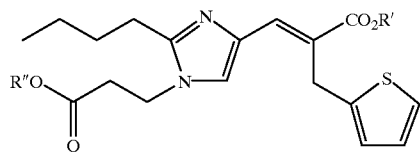
(Vb)

wherein R' and R" are as defined above, with a compound of formula (VI):

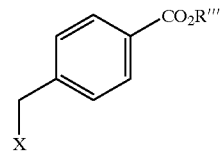
(VIb)

wherein R''' is $C_{1-4}$alkyl and X is halo, at elevated temperatures;

and thereafter hydrolyzing the R' and R''' ester groups and removing the N–3 protecting group, and optionally forming a pharmaceutically acceptable salt.

3. The process according to claim 1 for the preparation of eprosartan, a compound of formula (I):

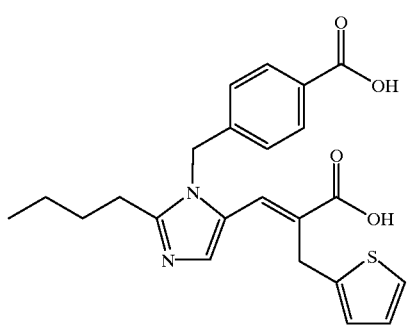
(I)

or a pharmaceutically acceptable salt thereof, which process comprises the steps of:

(i) treating a compound of formula (II):

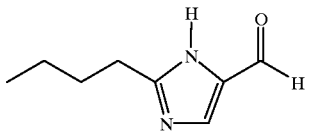
(II)

with 1,8-diazabicyclo[5.4.0]undec-7-ene, followed by reaction with methyl acrylate;

(ii) reacting the compound of formula (IIIa):

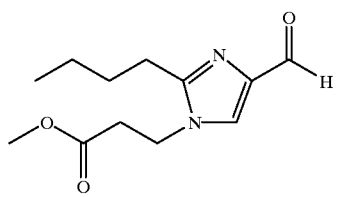
(IIIa)

with a compound of formula (IVa):

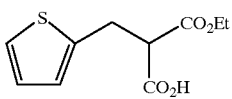
(IVa)

in the presence of piperidine; and (iii) reacting the compound of formula (Va):

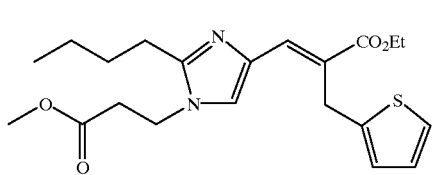
(Va)

with a compound of formula (VIa):

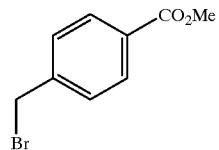
(VIa)

at elevated temperatures;

and thereafter hydrolyzing the ester groups and removing the N-3 protecting group, and optionally forming a pharmaceutically acceptable salt.

4. A process for the preparation of eprosartan, a compound of formula (I):

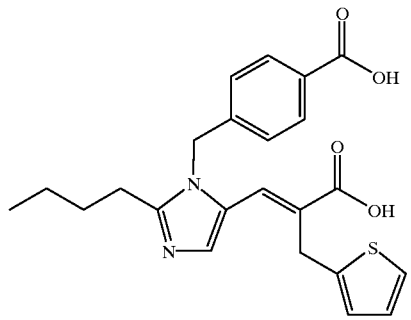
(I)

or a pharmaceutically acceptable salt thereof, which process comprises the steps of:

(i) reacting a compound of formula (II):

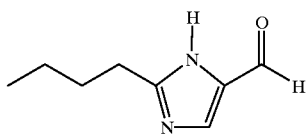
(II)

with a compound of formula (IV):

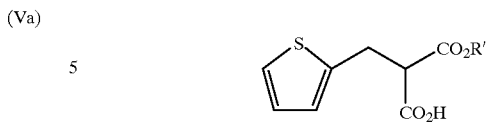
(IV)

wherein R' is $C_{1-4}$alkyl, in the presence of a catalyst;

(ii) treating the compound of formula (VII):

(VII)

with base, followed by reaction with a regioselective nitrogen-protecting reagent; and (iii) reacting the compound of formula (V):

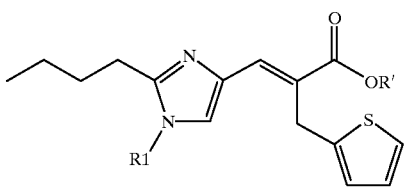
(V)

wherein R' is as defined above and R1 is a nitrogen protecting group either consisting of (1) an ethylene bridge connecting the nitrogen to an electron-withdrawing group, selected from the group consisting of an ester (COOR", wherein R"=$C_{1-4}$alkyl), acid, carbonyl, nitrile, sulfone, and sulfoxide, or (2) a methylene bridge connecting the nitrogen to a pivalate, 2-(trimethylsilyl) ethoxy, methoxy, tert-butoxy, or benzyloxy, with a compound of formula (VI):

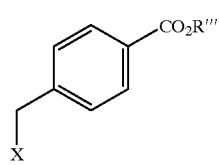
(VI)

wherein R''' is $C_{1-4}$alkyl and X is halo or OR*, in which R* is $CH_3SO_2$- or p-$CH_3C_6H_4SO_2$-, at elevated temperatures; and thereafter hydrolizing the R' and R''' ester groups and removing the N–3 protecting group, and optionally forming a pharmaceutically acceptable salt.

* * * * *